United States Patent [19]

Skaug et al.

[11] Patent Number: 6,114,155
[45] Date of Patent: Sep. 5, 2000

[54] INTERNAL CONTROL AND METHOD FOR SURVEILLANCE OF GAP-LCR

[75] Inventors: Kjell Skaug; Einar Sverre Berg, both of Oslo, Norway

[73] Assignee: Statens Institutt for Folkehelse, Oslo, Norway

[21] Appl. No.: 08/983,041

[22] PCT Filed: Jun. 26, 1996

[86] PCT No.: PCT/NO96/00158

§ 371 Date: Jan. 15, 1998

§ 102(e) Date: Jan. 15, 1998

[87] PCT Pub. No.: WO97/04128

PCT Pub. Date: Feb. 6, 1997

[30] Foreign Application Priority Data

Jul. 20, 1995 [NO] Norway .................................. 952881

[51] Int. Cl.[7] ................ C12P 19/34; C12Q 1/68
[52] U.S. Cl. ............... 435/91.52; 435/6; 435/91.2; 435/91.5; 435/91.51
[58] Field of Search ................ 435/6, 91.2, 91.5, 435/91.51, 91.52; 536/23.1

[56] References Cited

FOREIGN PATENT DOCUMENTS

| 0 465 435 | 1/1992 | Italy . |
|---|---|---|
| 0 609 573 | 8/1994 | Italy . |
| 93/02215 | 7/1992 | WIPO . |
| WO 93/02215 | 2/1993 | WIPO . |

OTHER PUBLICATIONS

Birkenmeyer et al., "Preliminary evaluation of the ligase chain reaction for specific detection of Neisseria gonorrhoeae", *J. Clin. Micro.*, 30:3089–94 (1992).

Abravaya, K. et al. Nucleic Acids Research 23(4):675–682, Feb. 1995.

*Primary Examiner*—Carla J. Myers
*Assistant Examiner*—Diana Johannsen
*Attorney, Agent, or Firm*—Gary M. Nath; Deborah H. Yellin; Nath & Associates

[57] ABSTRACT

A method for performing Gap-filling Ligase Chain Reaction (Gap-LCR) using an internal control which has been modified to contain a unique site for a restriction enzyme and which has approximately the same length and identical four LCR probe sites as the target nucleic acid.

7 Claims, 6 Drawing Sheets

TARGET

INTERNAL CONTROL

GAP-LCR AFTER ADDITION OF A NUCLEOTIDE TO THE INTERNAL CONTROL

⫽ :NICK TO BE SEALED BY DNA LIGASE

⇧ :INCORPORATION OF NUCLEOTIDE BY DNA POLYMERASE

TARGET

INTERNAL CONTROL

BgIII SITE (5'-A G A T C T -3')

GAP-LCR AFTER ADDITION OF A NUCLEOTIDE TO THE INTERNAL CONTROL

|/ : NICK TO BE SEALED BY DNA LIGASE

⇧ : INCORPORATION OF NUCLEOTIDE BY DNA POLYMERASE

TARGET

INTERNAL CONTROL

GAP-LCR AFTER DELETION OF A NUCLEOTIDE FROM THE INTERNAL CONTROL

|/ :NICK TO BE SEALED BY DNA LIGASE

⇧ :INCORPORATION OF NUCLEOTIDE BY DNA POLYMERASE

TARGET

GAP-LCR AFTER REPLACEMENT OF A NUCLEOTIDE IN THE INTERNAL CONTROL

|/ :NICK TO BE SEALED BY DNA LIGASE

⇧ :INCORPORATION OF NUCLEOTIDE BY DNA POLYMERASE

INTERNAL CONTROL AND METHOD FOR SURVEILLANCE OF GAP-LCR

The present invention concerns an internal control for use in the "gap-filing ligase chain reaction" (Gap-LCR). The internal control being a synthetic nucleotide, has substantially the same length and contains the hybridization sites for the same four LCR-probes as the target nucleic acid (the target sequence). The internal control and the target become accordingly amplified in a GAP-LCR with substantially the same effectiveness. Additionally the synthetic oligonucleotide is modified in the gap between the LCR-probes in such a way that it comprises a unique site for a restriction enzyme. Treatment of the LCR product with such a restriction enzyme will cut the internal control LCR product so that the LCR product from the target may be analyzed separately. The disclosed internal control may be used both in qualitative and quantitative LCR-based analysis.

BACKGROUND

Analyses based on enzymatic amplification of nucleic acids sometimes give false negative results e.g. on account of the presence of inhibitors in the samples. An inhibitor may for instance keep the enzymes from performing the reactions effectively. Samples containing inhibitors may be erroneously considered to lack a given target since their analyses does not give any signal. An addition of an internal control to the samples will reveal the presence of inhibitors since it is expected that the internal control always will be amplified and will give a signal. The internal control functions thus as a qualitative control.

The use of an internal control in polymerase chain reaction (PCR) based analyses has been disclosed by Matsumara et al. (Jpn. J. Clin. Oncol. 1992, 22:335–341). Their PCR with two sets of primers amplify a target of interest, but simultaneously another target functioning as an internal control in the reaction is amplified. Becker and Hahlbroeck (Nucl. Acid Res. 1989, 17:9437–9446) disclose a PCR based on a procedure wherein both target and internal control DNA is amplified by using the same two primers. Their internal control has become mutated in vitro so that it contains a unique site for a restriction enzyme. The PCR product from the internal control may be cleaved with the restriction enzyme and then be separated from the PCR product from the target by gel electrophoresis. Gilliland et al. (Proc. Natl. Acad Sci. USA 1990, 87:2725–2729) and Ursi et al. (APMIS 1992, 100:635–639) discloses internal controls which contain extra blocks of DNA between the PCR primer-sites. After PCR-amplification by using the same two primers the PCR-product from the internal control will have a different length than the target PCR product. These two may either be separated by gel electrophoresis or by hybridization with two selective probes. Also for "nucleic acid sequence amplification" (the NASBA system) there has been disclosed by Kievits and Lens (WO 94/04706) a procedure wherein both target and a longer/shorter internal control become amplified simultaneously by using the same primers.

Both the PCR and the NASBA internal controls may be used for quantitative analyses, for instance by densiometric measurements of the two bands appearing in gel electrophoresis of the amplification product.

So far ligase chain reaction (LCR) based analyses have lacked an internal control to be used in quantitative analyses. In a standard LCR disclosed by Backman (European Patent Office - 320.380 - 1987) the amplification of the target is being performed with only DNA ligase. In the reaction four probes are hybridised in pairs adjacent to each other on each strand in the target DNA. The nicks between the probes are closed by the DNA ligase so that two new DNA strands are produced. These may be used as a target in the next cycle of the process, see FIG. 1a.

The LCR internal control disclosed by Griffiths and Emery (WO 93/02215) has a different sequence than the target DNA on one side of the nick. The LCR amplification of the internal control requires thus the use of two extra LCR probes. These hybridise to the unique part of the control DNA, whereas the two LCR probes being common, hybridise to that part which is identical between the control and target DNA. In this way the nicks being ligated by the enzyme are being made. This has been shown schematically in FIG. 1b. The amplification products from the target and from the internal control may be separated e.g. by sequence specific hybridisation with selective probes. Even if this internal control may work as a qualitative control and reveal the presence of possible LCR inhibitors its effectivity in the amplification of the target and control DNA will be different on account of unequal sequences in the LCR probes. This limits the applicability and usefulness of such designed internal controls.

Figure 3A:
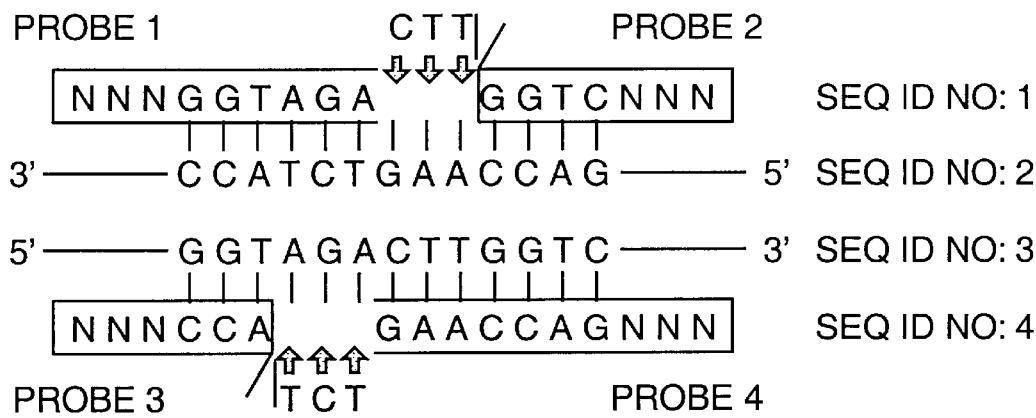
FIG. 3a–c shows examples of modifications in the control DNA with the purpose of creating a unique site for a restriction enzyme in the LCR product from the internal control. Only the polymerase step in the Gap-LCR process is indicated.
Figure 3A:
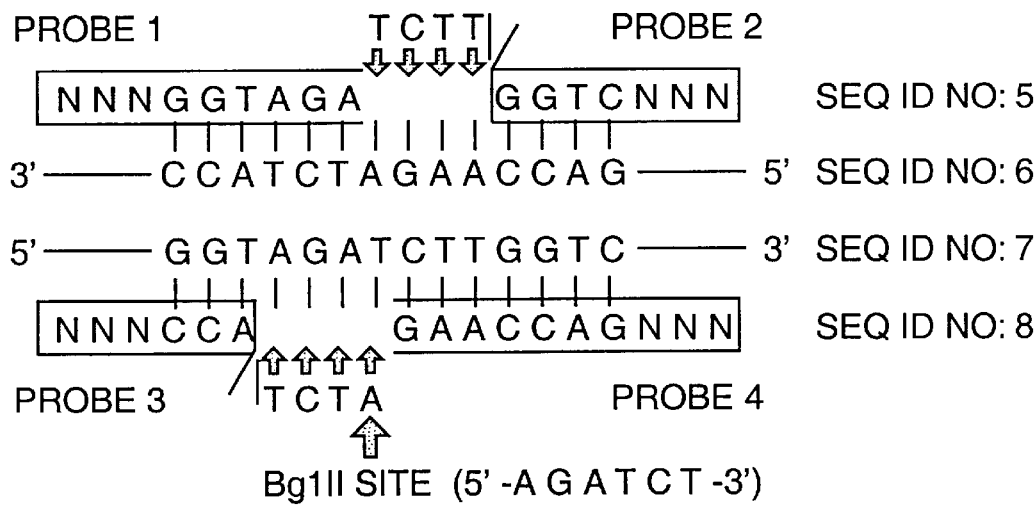

The top half of FIG. 3a shows probes 1 and 2 (SEQ ID NO:1) hybridized with the 3' strand of target DNA (SEQ ID NO:2) and the 5' strand of target DNA (SEQ ID NO:3) hybridization with probes 3 and 4 (SEQ ID NO:4). The bottom half of FIG. 3a shows probes 1 and 2 (SEQ ID NO:5) hybridization with the 3' strand of internal control DNA (SEQ ID NO:6) and the 5' strand of internal control DNA (SEQ ID NO:7) hybridization with probes 3 and 4 at a BgIII restriction site (SEQ ID NO:8).

Figure 3B:
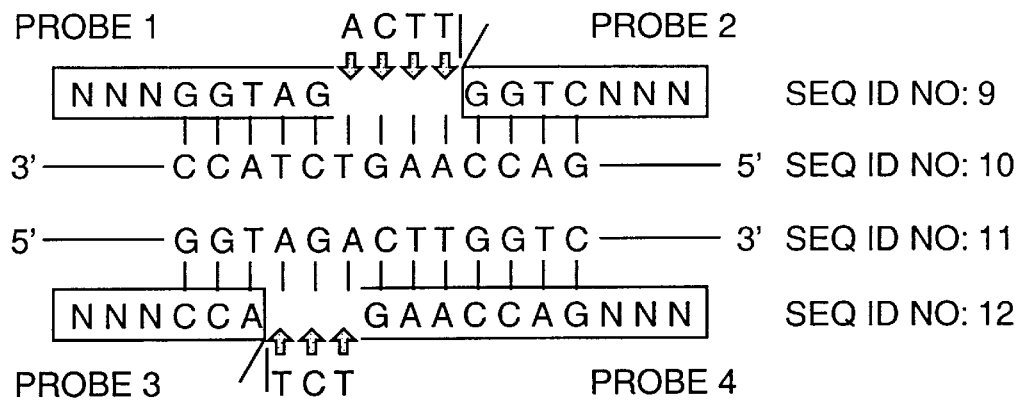
Figure 3B:
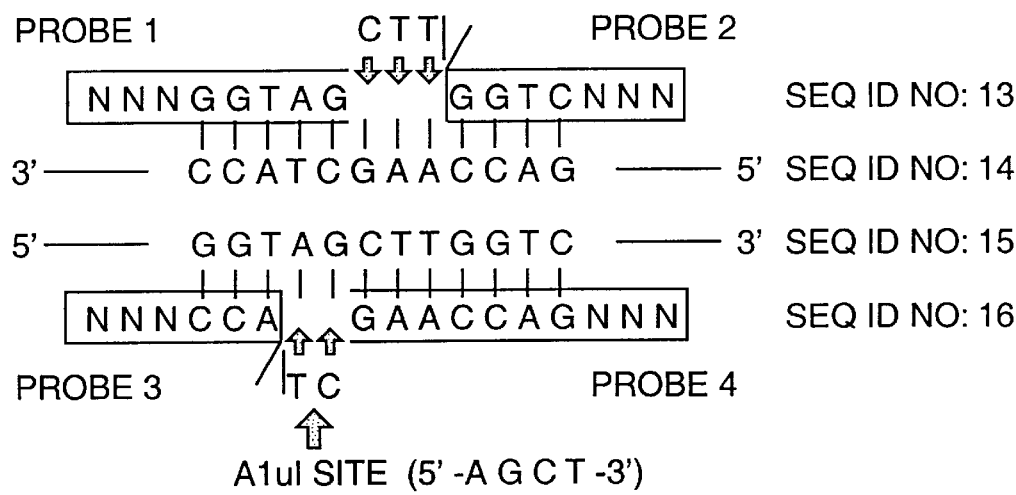

The top half of FIG. 3b shows probes 1 and 2 (SEQ ID NO:9) hybridization with the 3' strand of target DNA (SEQ ID NO:10) and the 5' strand of target DNA (SEQ ID NO:11) hybridized with probes 3 and 4 (SEQ ID NO:12). The bottom half of FIG. 3b shows probes 1 and 2 (SEQ ID NO:13) hybridization with the 3' strand of internal control DNA (SEQ ID NO:14) and the 5' strand of internal control DNA (SEQ ID NO:15) hybridized with probes 3 and 4 at a AluI restriction site (SEQ ID NO:16).

Figure 3C:
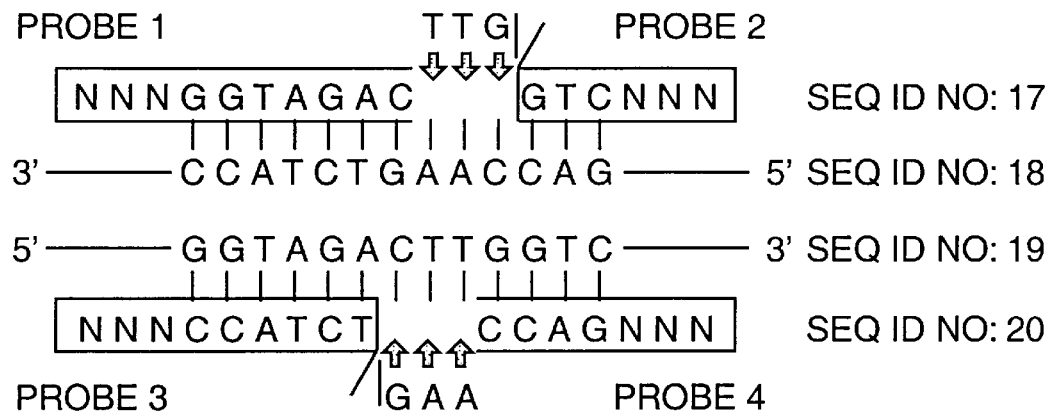
Figure 3C:
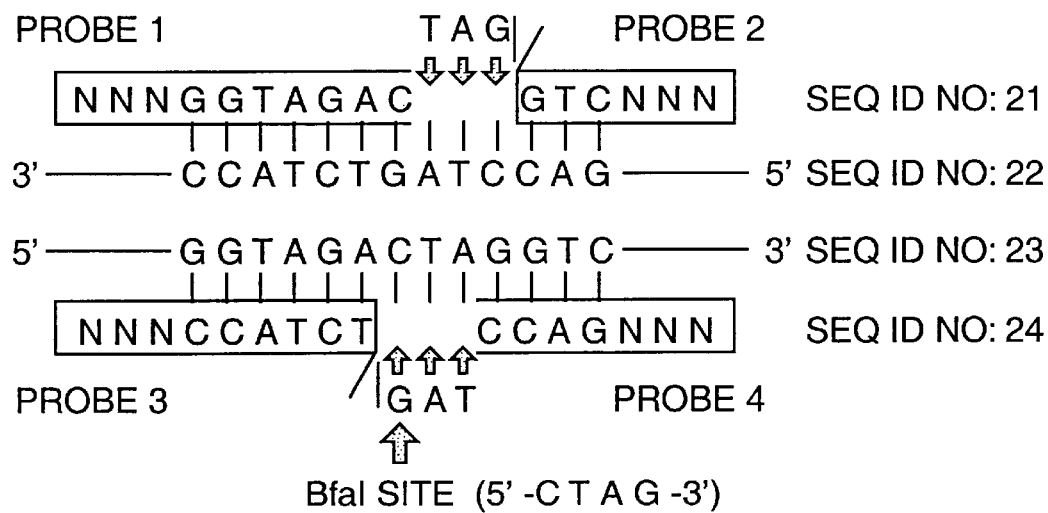

The top half of FIG. 3c shows probes 1 and 2 (SEQ ID NO:17) hybridized with the 3' strand of target DNA (SEQ ID NO:18) and the 5' strand of target DNA (SEQ ID NO:19) hybridized with probes 3 and 4 (SEQ ID NO:20). The bottom half of FIG. 3c shows probes 1 and 2 (SEQ ID NO:21) hyridized with the 3' strand of internal control DNA (SEQ ID NO:22) and the 5' strand of internal control DNA (SEQ ID NO:23) hybridized with probes 3 and 4 at a BfaI restriction site (SEQ ID NO:24).

Figure 1A:
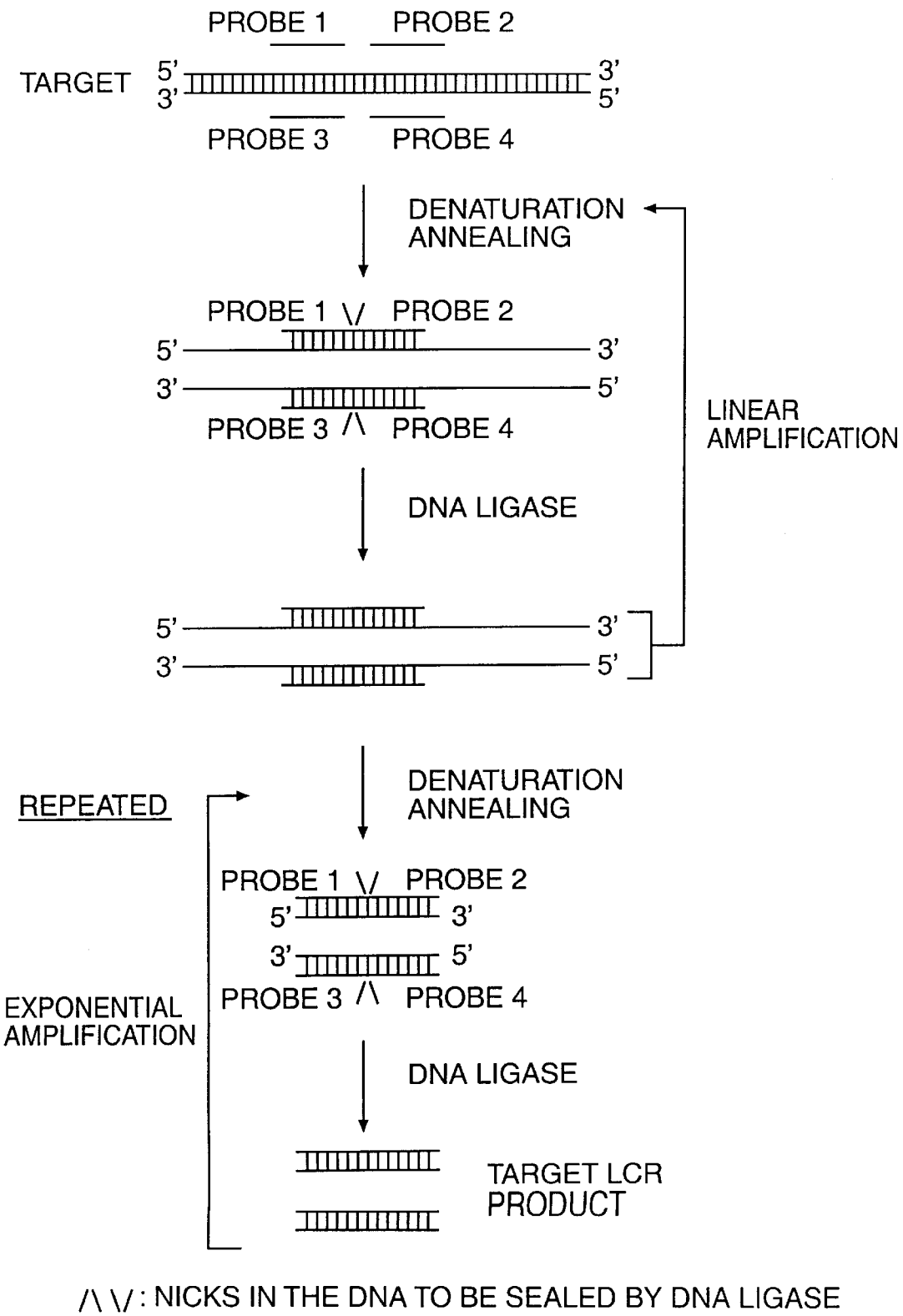
FIG. 1a is a schematical diagram of a standard LCR amplification.
Figure 1B:
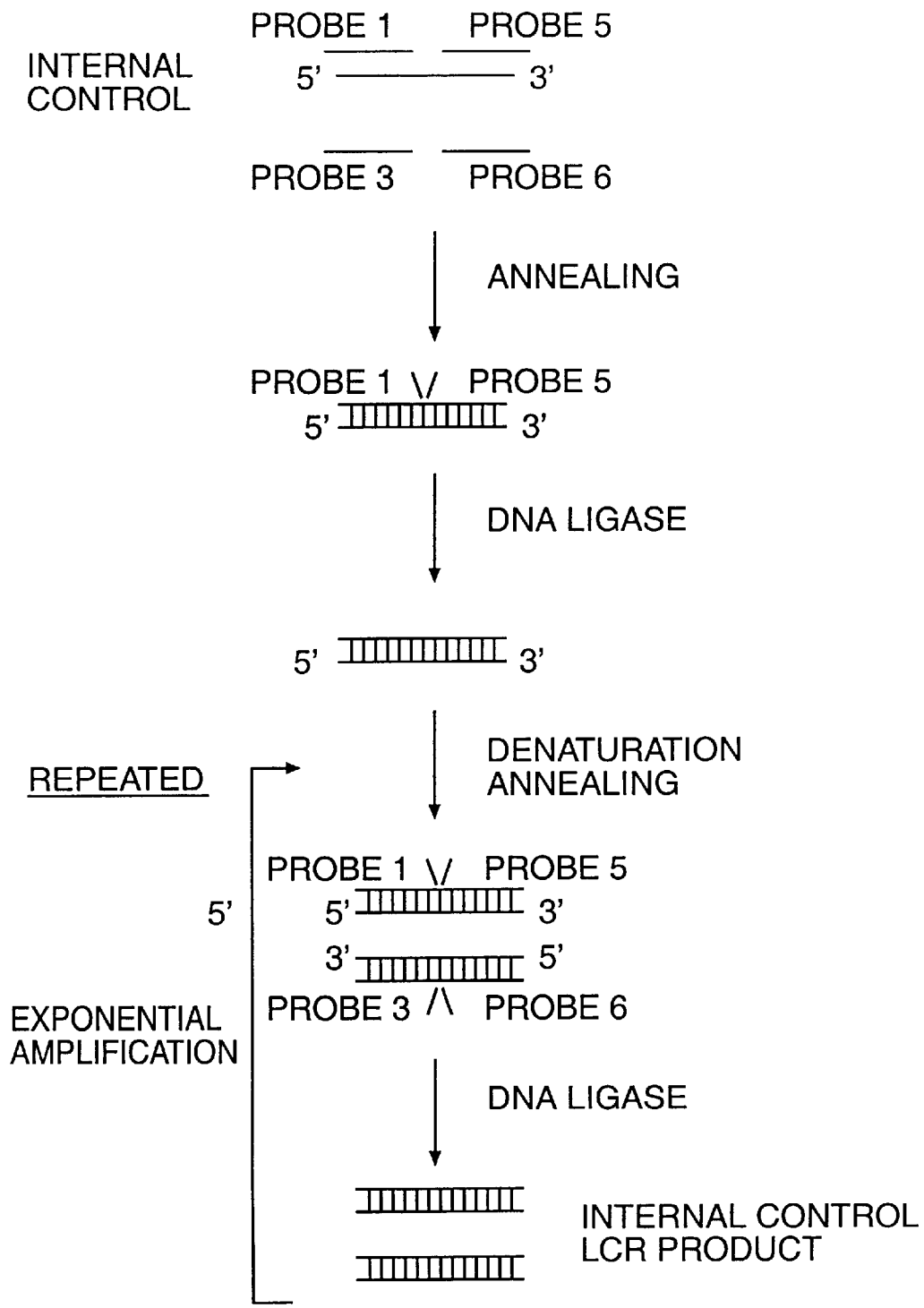
FIG. 1b shows the LCR amplification of an internal control wherein two extra probes are used as disclosed by Griffiths and Emery. Detection of the two LCR products may be done by hybridisation with selective probes an account of different sequences on the right side of the nicks.

In relation to FIG. 1a, please notice that the LCR of the internal control is being performed by using different probes as compared to the LCT of the target. The two LCR products get thus different sequences.

Figure 2:
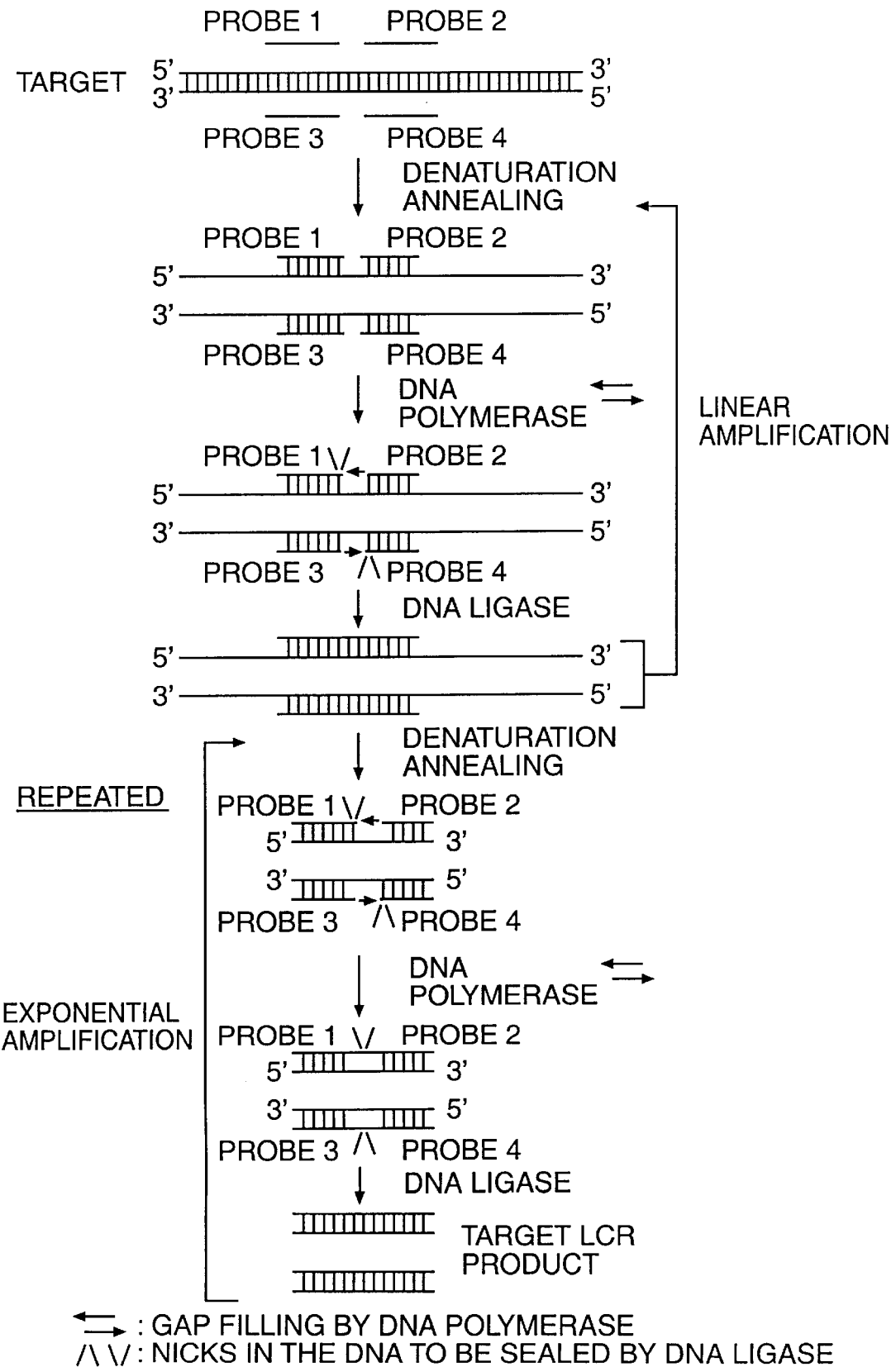
FIG. 2 is a schematic diagram depicting a gap-filling ligase chain reaction amplification (Gap-LCR) wherein both DNA polymerase and DNA ligase is used.

A modified LCR being disclosed by Backman et al (European Patent Office - 439.182A - 1991) gives an increased specificity. In this gap-filling LCR (Gap-LCR) two gaps arising between each of the probes in the two pairs of hybridised LCR probes are filled in with DNA polymerase before the ligation reaction may occur, see FIG. 2.

DISCLOSURE

The present invention concerns an internal standard to be used both in qualitative and in quantitative LCR-based analyses. It has the following basis: The gap between the probes in Gap-LCR allows some modification of the sequence in the gap, e.g. creation/deletion of a site for a restriction enzyme. This modification of the control DNA sequence is very limited and is dependent on the gap and probe sequences. This is in sharp contrast with the internal controls containing unique sites for restriction enzymes to be used in PCR. The modification of the Gap-LCR internal control sequence may comprise addition/deletion/exchange (see FIG. 3). of one or two deoxynucleoside triphosphates in addition to the base(s) which are necessary in the LCR of the target DNA. In PCR, on the other hand, a modification creating/deleting a site for a restriction enzyme is easily performed since there exist a relatively long distance between the PCR primers and all the four deoxynucleoside triphosphates which are present in the reaction. However, a larger modification of the control DNA in the Gap-LCR, which would lead to a need for all four the deoxynucleoside triphosphates to get the gap filled, would convert the LCR to a PCR. The amplification with the use of only DNA polymerase has significantly different reaction kinetics than the Gap-LCR wherein two enzymes, DNA polymerase and DNA ligase, are used. When the differences in sequence between the target and control DNA are small, the control DNA will be amplified in Gap-LCR with approximately the same effectivity as the target DNA. The amplification products from the present internal control and from the target DNA may be separated according to a simple treatment with restriction enzymes. This is the key to the present invention. The present internal control may thus function as both a qualitative and a quantitative internal standard for which there exists a need in qualitative enuring of LCR-based analyses, something which gives a significantly expanded area of use for such analyses.

With respect to FIG. 3a–c, the process indicated in this chart may obviously also be followed when removing a unique restriction site in the LCR product from the internal control DNA when target DNA contains a corresponding structure in its gap sequence.

EXAMPLE

The principle behind the present method is a construction of a nucleotide sequence in the internal control which is of mainly the same length and identical LCR probe sites as the target DNA. The internal control is designed with a unique site for a restriction enzyme in contrast with and as opposed to the target DNA. Accordingly the target and the internal control are amplified in Gap-LCR with approximately the same effectivity. A uniquely coding sequence from Hepatitis B virus (HBV) was chosen as a suitable target for the Gap-LCR amplification and for designing the internal standard.

Target Nucleic Acid Sequence (50 nucleotides)

The chosen HBV sequence contains the same sequences as the probes 1 and 3 joined together with -GCC- (the gap sequence). Notice that only one single DNA strand has been depicted in the figure.

Gap sequence

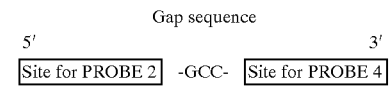

Internal control sequence (synthetic oligonucleotide) (51 nucleotides).

The sequence of the synthetic oligonucleotide (the internal control) is equal to the target nucleic acid sequence except for the gap sequence which has been modified to -GGCC-.

Gap sequence

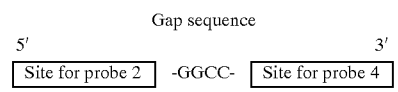

The nucleotide sequence for the synthetic oligonucleotide (the internal control) has a unique site for the restriction enzyme HaeIII (-GGCC-), whereas the sequence in the target does not. Thus when treating the amplified material with HaeIII, the amplified internal control will be cut whereas the amplified target remains unchanged.

Gap-LCR of Target (HBV sequence)

The probes 1 and 2 have been conjugated with carbazole (Ca) and the probes 3 and 4 with adamantane (Ad).

○ "Gap-filling reaction" (Dna polymerase); Ligation reaction (DNA ligase).

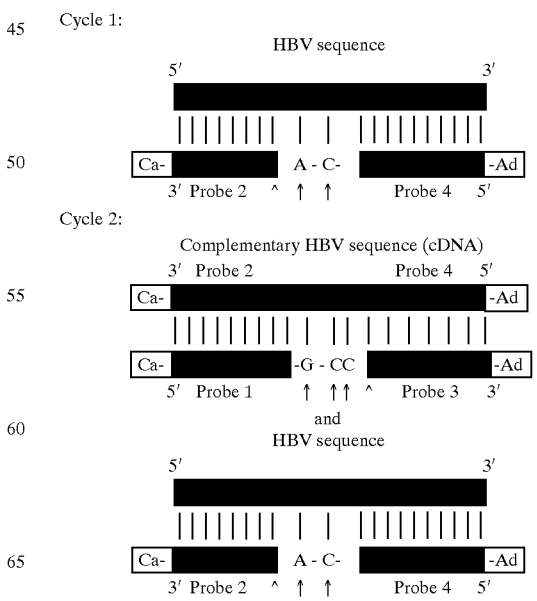

Gap-LCR of the Internal Control

The probes 1 and 2 have been conjugated with carbazole (Ca) and the probes 3 and 4 with adamantane (Ad). "Gap-filling reaction" (DNA polymerase); Ligation reaction (DNA ligase).

Cycle 1:
```
                    Internal control sequence
         5'                                          3'
         [================================================]
         |||||||| | || ||||||||||
         [Ca-]         A - CC-      [          -Ad]
         3' Probe 2    ^ ↑ ↑↑       Probe 4    5'
```

Cycle 2:
```
         Complementary internal control sequence (cDNA)
         3'  Probe 2                   Probe 4    5'
         [Ca-                                      -Ad]
         |||||||| || ||| | | | | |
         [Ca-          -GG - CC                    -Ad]
         5'  Probe 1   ↑↑  ↑ ↑ ^     Probe 3    3'
                              and
                    Internal control sequence
         5'                                          3'
         [================================================]
         |||||||| | || ||||||||||
         [Ca-]         A - CC-      [          -Ad]
         3' Probe 2    ^ ↑ ↑↑       Probe 4    5'
```

Repeat cycles (amplified product of internal control):
```
                          HaeIII
         3' Probe 2         ⇓         Probe 4   5'
         [Ca-                                    -Ad]
         |||||||| ||  |||||||||
         [Ca-                                    -Ad]
         5' Probe 1         ⇑         Probe 3   3'
                          HaeIII
```

The amplified internal control contains a unique site for the restrictions enzyme HaeIII. HaeIII cuts the LCR-product from the internal control in such a way that this may not be detected in the IMx-system which requires both carbazole and adamantane on one and the same DNA strand.

Detection of Amplified Material

The quantity of amplified product is measured by using the IMx-system (Abbott). The amplified material (target and internal control) reacts with particles coated with anti-carbazole. The quantity of bound material on the particles is detected by using anti-adamantane conjugated with alkaline phosphatase. This enzyme gives a colour response.

The amplified control contains a unique site for the restriction enzyme HaeIII (-CCGG-), whereas the amplified target DNA does not. After a mixture of the two LCR products have been treated with HaeIII, the quantity of amplified target may be measured alone. The difference in signal between the untreated (uncut) and the HaeIII-treated (cut) material gives the original quantity of target DNA in the sample by a simple ratio calculation, see infra. The disclosed method may accordingly be used both in qualitative and in quantitative Gap-LCR-based analyses.

Typical LCR-Results

The Gap-LCR was performed as described by Marchall et al. (PCR Methods and Applications, 1994, 4:80–84) with the following modifications: The 55 repeated cycles of the LCR comprised: Denaturing the double-stranded DNA at 85° C. followed by hybridisation/elongation/ligation at 55° C. The amplification was started by using a "Wax mediated Hot Start" and the denaturing of the first cycle lasted for 5 minutes.

Table 1: IMx-results of a synthetic control and a HBV-positive sample, untreated and treated with HaeIII (the original amount of synthetic control DNA: $10^3$ molecules).

| LCR product | IMx-rate |
| --- | --- |
| Synthetic control DNA | 206.0 |
| HaeIII-treated synthetic control DNA | 30.6 |
| Synthetic control DNA + HBV sample DNA | 922.1 |
| HaeIII-treated synthetic control DNA + HBV sample DNA | 857.7 |
| DNA negative control ($H_2O$ control sample) | 7.7 |
| HBV DNA negative control (serum sample) | 16.8 |

Positive/negative value: Imx rate 50.

Since the internal control and HBV DNA in the sample are amplified with approximately equal efficiency, the ratio between the control and the HBV DNA in the Gap-LCR process will be substantially constant during all cycles. The sensitivity level in the Gap LCR is shown in table 2, about 10 HBV DNA copies. By combining the DNA from the control and from the unknown sample, the HBV DNA from an unknown sample can be measured directly after the Gap-LCR and the HaeIII treatment, since the amount of control DNA is known.

Table 2: IMx test-results of different amounts of commercial standard ("Abbott positive control, hepatitis B viral DNA", $3 \times 10^7$ copies/ml)

| HBV copies | IMx-rate |
| --- | --- |
| 1500 | 446.0 |
| 15 | 75.6 |
| 0.15 | 20.2 |
| 0 | 14.2 |

Positive/negative value: IMx-rate 50

Specifically the present invention concerns a method for surveillance of the result of Gpa-LCR (Gapfilling Ligase Chain Reaction) wherein a target nucleic acid sequence enzymatically is amplified to yield amplification products, wherein an enzyme utilizes: a nucleic acid initiator, the target sequence or amplification product to which it hybridises as a template, and at least one additional nucleoside-containing reactant which can be enzymatically assembled to form amplification products which are complementary to the target sequence as well as a second enzyme acting on the amplified parts of the nucleic acid being hybridised to the template to combine the elongated part of the nucleic acid sequence with a second nucleic acid sequence probe, the constructed products serving as further templates for additional complementary nucleic acid sequences after dissociation from the target nucleic acid sequence, the improvement residing in that there is added to the reaction medium an extra target nucleic acid sequence as an internal control sequence, said internal control sequence being capable of hybridising to two nucleic acid sequences being present forming a gap between them, the sequence of extra target internal nucleic acid sequence being modified; to form or remove at least one (cleavage and/or attachment) site for a restriction endonuclease compared to the original target nucleic acid sequence, thus producing a substantially identical nucleic acid sequence as the target sequence, except for the introduced/removed modified site for a restriction endonuclease, whereupon the amplification product of the modified nucleic acid sequence is detected and optionally compared to the amplification product of the target sequence after digestion with a restriction endonuclease.

Furthermore, the improvement of the method according to the present invention resides in that the modification of the sequence in the gap comprises addition or deletion or replacement of at least one of the nucleotides.

Additionally, the method according to the present invention includes that at least one of the nucleosides of at least one of the sequences forming the probes in the LCR is modified to become detectable. Such a modification may involve adding at least one detectable compound to at least one of the nucleosides, said compound preferably, but not necessarily, being a protein, e.g. an antibody, an enzyme, a radioactive label, a substrate for a detectable enzymatic reaction, a chemiluminescent or phosphorescent substance, a detectable compound, e.g. a dye or a magnetic substance.

The method according to the present invention may be performed with a material wherein at least one of the nucleotide sequences comprises DNA. At least one of the nucleotide sequences may optionally comprise RNA.

The nucleoside sequence to be used as an internal control in the method according to the present invention, is a nucleoside sequence being able to hybridise to a complementary nucleoside sequence being elongated, forming or removing, when being combined with the second nucleoside sequence hybridising to the nucleoside sequence wherein the sequence of nucleosides in the internal control sequence is different from the target sequence, at lest one unique recognition and/or cleavage site for a restriction endonuclease.

The nucleoside sequence according to the present invention may furthermore comprise at least one nucleotide in the product from the internal control nucleoside sequence which is modified with at least one detectable compound such as a protein, e.g. an antibody, an enzyme, a radioactive label, a substrate for a detectable enzymatic reaction, a chemiluminescent or phosphorescent substance, a detectable compound, e.g. a dye or a magnetic substance.

The nucleoside sequence according to the present invention may include a nucleoside sequence comprising DNA or optionally RNA.

The Nucleoside sequence being disclosed supra and acting as an internal control in a LCR, my be included in a kit also comprising other reagents being required or preferred to perform a LCR.

The method and the nucleoside sequences according to the present invention may be used for both quantitative determination and qualitative surveillance of the progress and/or the results of a LCR, specifically Gap-LCR.

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Probes 1 and 2 for hybridization with 3' strand of
      target DNA, with the GAP filled in by polymerase
      and ligase.
<220> FEATURE:
<221> NAME/KEY: unsure
<222> LOCATION: (1)..(19)

<400> SEQUENCE: 1
nnnggtagac ttggtcnnn                                                      19

<210> SEQ ID NO 2
<211> LENGTH: 13
<212> TYPE: DNA
<213> ORGANISM: Hepatitis B virus
<220> FEATURE:

<400> SEQUENCE: 2
ccatctgaac cag                                                            13

```
<210> SEQ ID NO 3
<211> LENGTH: 13
<212> TYPE: DNA
<213> ORGANISM: Hepatitis B virus
<220> FEATURE:

<400> SEQUENCE: 3
ggtagacttg gtc                                                          13

<210> SEQ ID NO 4
<211> LENGTH: 19
<212> TYPE: DNA
<213> ORGANISM: Artificial Sequence
<220> FEATURE:
<220> FEATURE:
<221> NAME/KEY: unsure
<222> LOCATION: (1)..(19)

<400> SEQUENCE: 4
nnnccatctg aaccagnnn                                                    19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Probes 1 and 2
      for hybridization with the 3' strand of internal
      control DNA, with the GAP filled in by polymerase
      and ligase.
<220> FEATURE:
<221> NAME/KEY: unsure
<222> LOCATION: (1)..(20)

<400> SEQUENCE: 5
nnnggtagat cttggtcnnn                                                   20

<210> SEQ ID NO 6
<211> LENGTH: 13
<212> TYPE: DNA
<213> ORGANISM: Hepatitis B virus
<220> FEATURE:

<400> SEQUENCE: 6
ccatctagaa cca                                                          13

<210> SEQ ID NO 7
<211> LENGTH: 14
<212> TYPE: DNA
<213> ORGANISM: Hepatitis B virus
<220> FEATURE:

<400> SEQUENCE: 7
ggtagatctt ggtc                                                         14

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Probes 3 and 4
      to hybridize with the 5' strand of internal
      control DNA at a BgIII restriction site, with the
      GAP filled in by polymerase and ligase.
<220> FEATURE:
<221> NAME/KEY: unsure
<222> LOCATION: (1)..(20)
```

```
<400> SEQUENCE: 8
nnnccatcta gaaccagnnn                                            20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Probes 1 and 2
      to be hybridized to the 3' strand of the target
      DNA, with the GAP filled in by polymerase and
      ligase.
<220> FEATURE:
<221> NAME/KEY: unsure
<222> LOCATION: (1)..(19)

<400> SEQUENCE: 9
nnnggtagac ttggtcnnn                                             19

<210> SEQ ID NO 10
<211> LENGTH: 13
<212> TYPE: DNA
<213> ORGANISM: Hepatitis B virus
<220> FEATURE:
<220> FEATURE:

<400> SEQUENCE: 10
ccatctgaac cag                                                   13

<210> SEQ ID NO 11
<211> LENGTH: 13
<212> TYPE: DNA
<213> ORGANISM: Hepatitis B virus
<220> FEATURE:

<400> SEQUENCE: 11
ggtagacttg gtc                                                   13

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Probes 3 and 4
      to hybridize to the 5' strand of the target DNA,
      with the GAP filled in by polymerase and ligase.
<220> FEATURE:
<221> NAME/KEY: unsure
<222> LOCATION: (1)..(19)

<400> SEQUENCE: 12
nnnccatctg aaccagnnn                                             19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:  Probes 1 and
      2 to hybridize to the 3' strand of the internal
      control DNA, with the GAP filled in by polymerase
      and ligase.
<220> FEATURE:
<221> NAME/KEY: unsure
<222> LOCATION: (1)..(18)

<400> SEQUENCE: 13
nnnggtagct tggtcnnn                                              18
```

```
<210> SEQ ID NO 14
<211> LENGTH: 12
<212> TYPE: DNA
<213> ORGANISM: Hepatitis B virus
<220> FEATURE:

<400> SEQUENCE: 14
ccatcgaacc ag                                                              12

<210> SEQ ID NO 15
<211> LENGTH: 12
<212> TYPE: DNA
<213> ORGANISM: Hepatitis B virus
<220> FEATURE:
<220> FEATURE:

<400> SEQUENCE: 15
ggtagcttgg tc                                                              12

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Probes 3 and 4
      to hybridize to the 5' strand of internal control
      DNA having a AluI restriction site, with the GAP
      filled in by polymerase and ligase.
<220> FEATURE:
<221> NAME/KEY: unsure
<222> LOCATION: (1)..(18)

<400> SEQUENCE: 16
nnnccatcga accagnnn                                                        18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Probes 1 and 2
      to hybridize to the 3' strand of the target DNA,
      with the GAP filled in by polymerase and ligase.
<220> FEATURE:
<221> NAME/KEY: unsure
<222> LOCATION: (1)..(19)

<400> SEQUENCE: 17
nnnggtagac ttggtcnnn                                                       19

<210> SEQ ID NO 18
<211> LENGTH: 13
<212> TYPE: DNA
<213> ORGANISM: Hepatitis B virus
<220> FEATURE:

<400> SEQUENCE: 18
ccatctgaac cag                                                             13

<210> SEQ ID NO 19
<211> LENGTH: 13
<212> TYPE: DNA
<213> ORGANISM: Hepatitis B virus
<220> FEATURE:
```

```
<400> SEQUENCE: 19
ggtagacttg gtc                                                              13

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:      Probes
      3 and 4 to hybridize with the 5' strand of the
      target DNA, with the GAP filled in by polymerase
      and ligase.
<220> FEATURE:
<221> NAME/KEY: unsure
<222> LOCATION: (1)..(19)

<400> SEQUENCE: 20
nnnccatctg aaccagnnn                                                        19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Probes 1 and 2
      to hybridize to the 3' strand of the internal
      control DNA, with the GAP filled in by polymerase
      and ligase.
<220> FEATURE:
<221> NAME/KEY: unsure
<222> LOCATION: (1)..(19)

<400> SEQUENCE: 21
nnnggtagac taggtcnnn                                                        19

<210> SEQ ID NO 22
<211> LENGTH: 13
<212> TYPE: DNA
<213> ORGANISM: Hepatitis B virus
<220> FEATURE:

<400> SEQUENCE: 22
ccatctgatc cag                                                              13

<210> SEQ ID NO 23
<211> LENGTH: 13
<212> TYPE: DNA
<213> ORGANISM: Hepatitis B virus
<220> FEATURE:

<400> SEQUENCE: 23
ggtagactag gtc                                                              13

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Probes 3 and 4
      for hybridization to the 5' strand of the internal
      control DNA with a BfaI restriction site, with the
      GAP filled in by polymerase and ligase.
<220> FEATURE:
<221> NAME/KEY: unsure
<222> LOCATION: (1)..(19)
```

```
<400> SEQUENCE: 24
nnnccatctg atccagnnn                                                19
```

What is claimed is:

1. A method for performing Gap-LCR (Gapfilling Chain Reaction) which comprises:
   a) forming a reaction medium comprising a target nucleic acid sequence, a DNA polymerase, a first nucleic acid sequence probe, a second nucleic acid sequence probe, a ligating enzyme selected from ligase or an enzyme with a ligase function, and at least one additional nucleoside-containing reactant, wherein said target nucleic acid sequence comprises a gap sequence which is flanked on one side by a region complementary to said first nucleic acid sequence probe and on the other side by a region complementary to said second nucleic acid probe;
   b) adding to the reaction medium an internal control sequence comprising a gap sequence flanked on one side by a region complementary to said first nucleic acid sequence probe and on the other side by a region complementary to said second nucleic acid probe, wherein the gap sequence in the internal control sequence differs from the gap sequence in the target nucleic acid sequence such that the internal control sequence either contains a restriction endonuclease site not found in the target nucleic acid sequence, or lacks a restriction endonuclease site found in the target nucleic acid sequence;
   c) amplifying the target nucleic acid sequence and the internal control sequence using the first nucleic acid sequence probe and the second nucleic acid sequence probe, wherein during amplification the first probe and the second probe hybridize to said regions complementary to said first and second probes in both the target nucleic acid sequence and the internal control sequence;
   and
   d) detecting amplification products produced in step c), wherein internal control sequence amplification products either contain a restriction endonuclease site not found in target nucleic acid sequence amplification products, or lack a restriction endonuclease site found in target nucleic acid sequence amplification products; and
   e) optionally, comparing internal control sequence amplification products with target nucleic acid sequence amplification products by digesting amplification products with a restriction endonuclease.

2. The method of claim 1, wherein the gap sequence in the internal control sequence differs from the gap sequence in the target nucleic acid sequence in containing at least one more nucleotide than the gap sequence in the target nucleic acid sequence, in containing at least one less nucleotide than the gap sequence in the target nucleic acid sequence, or in containing at least one substituted nucleotide with respect to the gap sequence in the target nucleic acid sequence.

3. The method of claim 2, wherein at least one of the amplification products formed in step c) is detectably labeled.

4. The method of claim 3, wherein the first nucleic acid sequence probe, the second nucleic acid sequence probe, or the at least one additional nucleoside-containing reactant is labeled with a detectable material selected from the group consisting of a protein, an antibody, an enzyme, a radioactive label, a substrate for a detectable enzyme reaction, a chemiluminescent or phosphorescent substance, a dye, and a magnetic substance.

5. The method of claim 1, wherein at least one of the target nucleic acid sequence, the internal control sequence, the first nucleic acid sequence probe, the second nucleic acid sequence probe, or the at least one additional nucleoside-containing reactant comprises DNA.

6. The method of claim 1, wherein at least one of the target nucleic acid sequence, the internal control sequence, the first nucleic acid sequence probe, the second nucleic acid sequence probe, or the at least one additional nucleoside-containing reactant comprises RNA.

7. The method of claim 1, wherein at least one internal control sequence amplification product formed in step c) is detectably labeled with at least one detectable material selected from the group consisting of a protein, an antibody, an enzyme, a radioactive label, a substrate for a detectable enzyme reaction, a chemiluminescent or phosphorescent substance, a dye, and a magnetic substance.

* * * * *